United States Patent [19]

Lemole

[11] Patent Number: 5,019,604

[45] Date of Patent: May 28, 1991

[54] PROTECTIVE GEL COMPOSITION

[76] Inventor: Gerald M. Lemole, 404 Tomlinson Rd., Huntingdon Valley, Pa. 19006

[21] Appl. No.: 343,417

[22] Filed: Apr. 26, 1989

[51] Int. Cl.$^5$ ............................................. A61K 31/74
[52] U.S. Cl. ..................................... 523/105; 424/78; 424/81; 424/445; 424/447; 514/969
[58] Field of Search ..................... 424/DIG. 5, 78, 81; 514/562; 523/105

[56] References Cited

U.S. PATENT DOCUMENTS

| | | | |
|---|---|---|---|
| 3,100,180 | 8/1963 | Smith et al. | 424/78 |
| 3,541,205 | 11/1970 | Hardigan | 424/78 |
| 3,824,218 | 7/1974 | McKenna et al. | 424/78 |
| 3,872,040 | 3/1975 | Mollohan et al. | 428/458 |
| 4,035,506 | 7/1977 | Lucas et al. | 514/562 |
| 4,478,853 | 10/1984 | Chaussee | 424/DIG. 5 |

FOREIGN PATENT DOCUMENTS 0105657 9/1983 European Pat. Off. .
0255902 2/1988 European Pat. Off. .

OTHER PUBLICATIONS

Condensed Chemical Dictionary, 8th edition, pp. 396; 849.

Primary Examiner—Thurman Page
Assistant Examiner—James M. Spear
Attorney, Agent, or Firm—Armand M. Vozzo, Jr.

[57] ABSTRACT

A protective gel composition is disclosed for coating skin surfaces, particularly the hands of the surgical attendants prior to covering the hands with standard surgical gloves. In one example, the composition comprises controlled proportions in mixture by weight of lanolin, a liquid silicone, polypropylene glycol monooleate, polytetrafluoroethylene powder in microspherical form and zinc oxide powder. Anti-microbial and anti-viral agents may be further added to fortify the coating of the composition, with a preferred such agent being nonoxynol-9. The sterilized composition is applied to the hands after scrubbing and just prior to insertion into the gloves. The coating is water-repellent to prevent skin contact with body fluids, such as blood and blood products, that may penetrate the gloves and otherwise expose the skin to harmful microbial and viral infections. When the gloves are removed following the surgical procedure, the coating is easily removed with an alcohol and liquid detergent wash.

17 Claims, No Drawings

PROTECTIVE GEL COMPOSITION

BACKGROUND OF THE INVENTION

The present invention relates to protective gel compositions for coating the skin and more particularly to an improved protective gel having water-repellent qualities especially useful as a skin shield on the hands of medical personnel wearing surgical gloves.

Medical personnel attending to a surgical procedure are at great risk to come into contact with patient blood. A serious danger exists with such exposure in the event the blood is infectious and comes into immediate contact with the skin of the attendant personnel. Surgical gloves and other body covering traditionally worn to maintain a sterile environment in operating rooms can also provide a certain barrier to an infectious exposure to blood from the surgical patient having hepatitis or Acquired Immune Deficiency Syndrome (AIDS). Surgical gloves, however, may have microscopic holes or openings therein that either occur in their manufacture or which can form shortly after first use. Those microscopic holes occurring during glove manufacture are extremely difficult to detect, while those occurring during use will not generally be known, if at all, until after harmful exposure has been effected. Inasmuch as the hands of the surgical attendants may possess abrasions or cuts that provide a source of entry for the infectious disease, it is essential that the hands of those attendants be afforded greater protection than that provided by standard surgical gloves.

In a typical operating room scenario, the undetected holes that occur in surgical gloves are only recognized by evidences of blood upon the hands of the surgical attendant after the surgical procedure is completed and the gloves have been removed. Indeed, health professionals are much more likely to come into contact with contaminated blood in this manner than by a needle stick, since personnel often have minute cuts, abrasions, and skin rashes which can be a portal of entry. In such working environments, therefore, it is imperative that a protective coating be applied to the hand surfaces beneath standard surgical gloves as a shield against skin contact from blood and blood products that may penetrate the gloves and otherwise cause infection of personnel. Most desirable in a gel form, such a protective coating should be sterilizable, nontoxic, maintain its physical properties at body temperature, be hydrophylic and water insoluble. It should further be non-reactive with the latex rubber of conventional surgical gloves, act as a lubricant during hand insertion into the gloves, remain on the site of application for several hours during any procedure, and be readily removed thereafter.

While numerous protective gel compositions have been developed for topical application to the skin, such compositions have generally been used for the temporary treatment of surface wounds, providing a water-soluble coating impermeable to air-ridden germs and bacteria. While these water-soluble compositions have provided satisfactory protective coatings that prevent germs and bacteria in the air from reaching the skin surface, they have not provided adequate protection from the biochemical hazards carried by blood and blood products to which the hands of the surgical attendants are constantly exposed in the operating room environment.

SUMMARY OF INVENTION

Accordingly, it is a general purpose and object of the present invention to provide an improved protective coating gel that effectively shields the skin and mucosa from exposure to infectious diseases.

Another object of the present invention is to provide a protective gel composition that coats the hands of surgical attendants beneath their gloves forming an impermeable barrier to biological hazards that may penetrate the gloves during surgical procedures.

Still another object of the present invention is to provide a sterilizable protective gel that is hypo-allergenic to the skin surface to which it is applied and non-reactive to the glove or other covering material worn over the skin.

An additional object of the present invention is to provide a protective gel that is sterilizable, hydrophylic, and water-insoluble, and further able to coat and fill in scratches, cuts, abrasions, and other disorders that create a break in the skin continuity.

A further object of the present invention is to provide a protective gel composition that adheres well to the skin surface while also serving as a useful lubricant thereon for the placement of surgical gloves or other covers over the skin surface to be protected.

A still further object of the present invention is to provide a protective gel that is safe to apply to the skin, easy to remove after use, and economical to manufacture.

Briefly, these and other objects of the present invention are accomplished by a protective gel composition for coating skin surfaces, particularly the hands of surgical attendants prior to covering the hands with standard surgical gloves. In one working example, the composition comprises controlled proportions in mixture by weight of lanolin, liquid silicone, polypropylene glycol mono-oleate, a powder of polytetrafluoroethylene in microspherical form, and a zinc oxide powder. Antimicrobial and anti-viral agents may be further added to fortify the coating of the composition, a preferred such agent being nonoxynol-9. The sterilized composition is applied to the hands after scrubbing and just prior to insertion into the gloves. The coating is water-repellent to prevent skin contact with body fluids, such as blood and blood products, that may penetrate the gloves and otherwise expose the skin to harmful microbial and viral infections. When the gloves are removed following the surgical procedure, the coating is easily removed with an alcohol and liquid detergent wash.

Other objects, advantages and novel features of the present invention will become apparent from the following detailed description thereof.

DESCRIPTION OF THE PREFERRED EMBODIMENT

The present invention is a water-insoluble gel composition intended to be used as a protective coating for skin surfaces, particularly those of the hands, which are at risk of exposure to body fluids, such as blood and blood products, during a medical or surgical procedure. Since those skin surfaces at risk are generally covered with surgical gloves or the like in order to provide skin protection and maintain a sterile environment, the protective coating of the present gel composition is applied directly upon the skin surface just prior to covering and thus serves as an intermediate barrier against hazardous infections carried by the body fluids that may penetrate the glove cover. As such a barrier, the present coating also prevents resident bacteria in the skin pores of the attendant medical personnel from coming into contact with the sterile field through a microscopic hole in the glove.

In accordance with the present invention and the variety of working examples set forth below, the protective gel composition invention comprises a mixture of lanolin, liquid silicone, polypropylene glycol mono-oleate, and polytetrafluoroethylene powder in microspherical form, each ingredient of which may be contained in a respective range of percentages by weight as detailed and explained below. An amount of zinc oxide powder, in percentages by weight detailed in selected examples hereinbelow, may also be included in the present protective gel composition. In a further aspect of the invention, certain medicaments may be added to the composition as aforedescribed in order to specifically fortify the protective coating as a barrier against certain infectious carriers. Such medicaments which can be incorporated in the present gel composition include for instance, anti-bacterial and anti-viral agents, such as nonoxynol-9 and povidone. The concentrations of medicaments in the composition when prepared will vary depending upon the particular medicament employed, but in all instances will be an amount effective for the intended purpose. The nonoxynol-9 is the medicament particularly preferred in the present composition based on its known effectiveness in inactivating HIV replication and the transmission of associated HIV infections. The effective range of the nonoxynol-9 in the present protective gel composition is between about 0.025% and about 1.0% by weight. In the case of povidone, on the other hand, the amount contained as a medicament in the protective gel composition of the present invention will range below about 10%, preferably between about 5.0% and about 8.0% by weight.

In regard to the specific ingredients contained in the present gel composition, the lanolin serves as a water-insoluble base and comprises a major portion of the total composition, its proportion being in the preferred range of about 50% to 90% by weight. The lanolin specifically employed is substantially pure in nature and commercially available in gel form. Generally produced from the grease of the wool of sheep, the lanolin employed herein is a cosmetically acceptable wax, as such is known and characterized by water insolubility, hydrophylia, non-toxicity and inertia at body temperature. Other cosmetically acceptable waxes, of animal, mineral or plant origin, having similar physical and chemical characteristics as that of lanolin may be substituted therefor in like proportional amounts to serve as the water-insoluble base of the protective gel composition. Suitable substitutes for lanolin from this category of cosmetically acceptable wax ingredients would be paraffin, carnauba wax, beeswax, mineral wax, cocoa butter and petrolatum. Additionally, synthetic substitutes for the lanolin having cosmetic characteristics similar thereto may be usefully employed in the protective gel composition of the present invention. For example, the combination of a polymerized hydrophylic acrylate and low-chain alcohol emollient provide a suitable substitute for lanolin in the present composition.

The liquid silicone referred to herein and employed in the gel composition of the present invention is a fluid from the group of organo-silicone polymers, also known as polysiloxanes. This well known class of compounds, often referred to as "silicones" is commonly used in cosmetic preparations, offering properties of water repellency, slip, non-greasy emollience and low penetration of the skin. Such polysiloxane fluids are generally insoluble in water and are available in viscosities ranging from about 40 to about 100,000 centistokes at 25° C. In the present composition, the liquid silicone functions primarily as a water-repellent agent and further provides the protective gel with sufficient characteristics of lubricity, sterilizability, inertia, non-toxicity and heat stability. In the present invention, the liquid silicone comprises a minor portion of the total composition, its proportion being below about 10% by weight. A more limited range of the liquid silicone found effective in the working examples set forth below is between about 3% and 6% by weight. A particular such liquid silicone preferred for use in the present composition is a dimethylpolysiloxane fluid, a suitable example of which is a commercially available product from the General Electric Co. known as "GE SF-96 Silicon Oil". Other water-repellent compounds from the group of organo-silicone polymers having the same or similar physical characteristics as that of the described liquid silicone may be combined used in combination with the silicone or as a substitute therefor in the present protective gel composition.

The polypropylene glycol mono-oleate referred to herein and employed in the present protective gel composition is a commercially available surfactant in the chemical group of polypropylene glycol fatty acid esters. Employed in the present composition as a surface active agent serving particularly as a spreading aid, dispersant and emollient, the polypropylene glycol mono-oleate is a clear, light-colored liquid of relatively low viscosity, typically in the range of about 270 cps (Brookfield RVF) at 25° C. This surfactant further exhibits high lubricity and good spreadability without being of a greasy or tacky nature. The polypropylene glycol mono-oleate is soluble in common alcohols and certain water/alcohol solutions, but generally is insoluble in water at 25° C. Other typical properties include an Acid Number of 1.3, Saponification Number of 25.0, and a Specific Gravity of 0.99 at 25° C. A suitable such polypropylene glycol mono-oleate for use in the present composition is "WITCONOL F26-46" manufactured by the Organics Division of Witco Chemical Corporation. Other polypropylene glycols that exhibit similar chemical and physical properties to the described mono-oleate may serve as a substitute therefor in the present gel composition. Similarly, stearic acid may be a suitable alternative to the polypropylene glycol mono-oleate as a surface-active agent in the present composition.

The polytetrafluoroethylene powder referred to herein and employed in the present invention is a commercially known and available product that serves the composition particularly as a nonwetable lubricating agent as well as a particulate for filling crevices on the applied skin surface in aid of adhesion. Preferred for use in a microspherical form, the polytetrafluoroethylene powder comprises about 2% to 10% by weight of the present composition. A suitable polytetrafluoroethylene powder for use in the present composition is that of "TEFLON", manufactured by the DuPont Company.

The zinc oxide referred to herein is a white, commercially available non-toxic powder that serves in the present composition as a pigment as well as an adherent that binds the ingredients and provides the coating with good adhesion qualities upon the skin surface to which it is applied.

Specific formulations of the protective gel composition are set forth below in respectively numbered examples, each on a weight percent basis.

EXAMPLE 1

| Lanolin | 83.8% |
|---|---|
| Liquid Silicone - Dimethylpolysiloxane | 3.0% |
| Polytetrafluoroethylene powder | 5.0% |
| Zinc Oxide powder | 7.7% |
| Nonoxynol-9 | 0.5% |

The foregoing formulation of the present composition is prepared by warming the lanolin to just beyond its melting point or to about 50° C. and adding the zinc oxide powder. As the temperature is maintained and while thoroughly mixing, the polytetrafluoroethylene powder is added until uniformly dispersed. To this mixture, the liquid silicone is added and further mixed together before allowing the composition to cool to ambient temperature at which a firm, creamy yellow gel is formed. The desired amount of medicament (nonoxynol-9 in the example above) may then be added to the gel composition prior to its sterilization, typically by gamma irradiation.

EXAMPLE 2

| Lanolin | 69.5% |
|---|---|
| Polypropylene glycol mono-oleate | 11.0% |
| Polytetrafluoroethylene powder | 6.0% |
| Zinc Oxide powder | 6.0% |
| Povidone | 7.5% |

This second formulation of the protective gel composition is prepared in like manner to that formulation of Example 1, with the povidone being added as a medicament in substantially greater amount than the nonoxynol-9 of the first formulation.

EXAMPLE 3

| Lanolin | 71.75% |
|---|---|
| Liquid Silicone - Dimethlypolysiloxane | 6.0% |
| Polypropylene glycol mono-oleate | 10.0% |
| Polytetrafluoroethylene powder | 6.0% |
| Zinc Oxide powder | 6.0% |
| Nonoxynol-9 | 0.25% |

This formulation is similarly prepared to that of the previously described examples, with the liquid silicone and polypropylene glycol mono-oleate being added together and mixed in respective proportions prior to addition of the nonoxynol-9 medicament.

EXAMPLE 4

| Lanolin | 80.0% |
|---|---|
| Liquid Silicone - Dimethypolysiloxane | 5.0% |
| Polypropylene glycol mono-oleate | 10.0% |
| Polytetrafluoroethylene powder | 5.0% |
| Nonoxynol-9 | 0.05% |

The above formulation proved to have most effective results as a protective coating gel, being prepared similarly to that of Example 3 but without inclusion of the zinc oxide powder.

In accordance with the method of the present invention, the prepared gel composition is first sterilized and then applied by hand to the skin surface to be protected so that a thorough coat is applied. The required sterilization would be effected by conventional methods, typically by gamma irradiation or gas sterilization techniques. Typically, such application of the gel coating will occur upon the hands of surgical personnel in a sterile operating room environment immediately after the hands are scrubbed. The hands, coated with the protective gel, are then inserted into standard surgical gloves to provide the personnel with the additional protective physical and biochemical barrier of the gel coating during intra-operative use.

Beneath the covering of the surgical glove, the present gel composition provides a sterile, water-insoluble coating for the skin that does not dissolve or otherwise breakdown the conventional glove materials of latex rubber and the like. The coating is relatively thin but effective as a repellent barrier to water-based body fluids, such as blood and blood products, that may possibly penetrate the glove cover and carry bacterial or viral infections to the skin. Upon the skin surface and covered by the gloves, the coating of the present composition remains consistent and of gel-like viscosity, with the composition not liquifying or otherwise breaking down at the body temperature levels reached during use. At the end of the surgical procedure following the removal of the glove cover, the coating is easily wiped and cleaned from the skin by washing with alcohol and liquid detergent.

Therefore, some of the many advantages of the present invention should now be apparent. Generally, the described protective gel composition probides an improved coating that effectively shields the skin of medical personnel for several hours from harmful contact with body fluids and the consequent exposure to infectious diseases. More particularly, the present protective gel composition especially serves to coat the hands of surgical attendants beneath their gloves thereby forming an impermeable barrier to microbial and viral hazards that may penetrate the gloves during surgical procedures. The described protective gel is sterilizable for appropriate surgical use and is compatible with various medicaments, anti-bacterial and anti-viral, that fortify the protective coating. Additionally, the present protective gel is hypoallergenic to the skin surface to which it is applied and non-reactive to the surgical gloves or other coverings material worn over the skin. The coating provided by the present gel composition adheres well to the skin surface while also providing a useful lubricant that facilitates the placement of the skin cover used over the surface being protected. The protective gel is safe and easy to apply, readily washable with alcohol and liquid detergent and economical to manufacture.

Obviously, any modifications and variations of the present invention are possible in light of the above teachings. For example, in addition to its employ as a skin coating to be applied beneath surgical gloves, the present protective gel composition can be effectively used as an ointment to be used in conjunction with condoms to protect the skin and mucosa from microbial and viral hazards. Furthermore, rather than being topically applied by the user upon the skin surface to be protected, the present gel composition may be provided as an inner coating layer in the manufacture of the surgical glove or other skin covering and thus be intimately applied to the skin concurrently with the placement of the gloves or other coverings. It is therefore to be understood that, within the scope of the appended claims, the invention may be practiced otherwise than as specifically described.

What is claimed is:

1. A sterilizable water-insoluble gel useful as a protective coating for skin and mucosa, comprising:
   about 50-90% by weight of lanolin as a water-insoluble base;
   an amount of liquid silicone effective as a water-repellent agent;
   an amount of a polypropylene glycol fatty acid ester effective as a surfactant; and
   a polytetrafluorethylene powder in microspherical form as lubricating agent.

2. A gel according to claim 1, further comprising:
   an amount of zinc oxide powder effective as a binding agent.

3. A gel according to claim 1, further comprising:
   an amount of a medicament effective to fortify the gel against selected bacterial and viral infections.

4. A gel according to claim 3, wherein:
   said major portion of lanolin is from about 50% to about 90% by weight;
   said amount of said liquid silicone is below about 10% by weight;
   said amount of said polypropylene glycol fatty acid ester is up to about 10% by weight; and
   said polytetrafluorethylene powder is contained in the range of about 2% to about 10% by weight.

5. A gel according to claim 4, wherein said medicament is nonoxynol-9.

6. A gel according to claim 5, wherein said nonoxynol-9 is contained in the range of about 0.025% to about 1% by weight.

7. A gel according to claim 4, wherein said medicament is povidone.

8. A gel according to claim 7, wherein said povidone is contained in the range of about 5% to about 8% by weight.

9. A gel according to claim 4, wherein said liquid silicone is a polysiloxane fluid.

10. A gel according to claim 9, wherein said polysiloxane fluid is dimethylpolysiloxane.

11. A gel according to claim 4, wherein said polypropylene glycol fatty acid ester is polypropylene glycol mono-oleate.

12. A sterilizable water-insoluble gel useful as a protective coating for skin and mucosa covered by a glove-like member, comprising:
    about 50% to 90% by weight of a cosmetically acceptable wax as a water-insoluble base;
    up to about 10% by weight of a liquid silicone as a water-repellent agent;
    about 2% to 10% by weight of a polytetrafluoroethylene powder in microspherical form;
    up to about 10% by weight of a polypropylene glycol fatty acid ester as a surfactant;
    an amount of a zinc oxide powder effective as a binding agent; and
    a sufficient amount of a medicament to fortify the gel against selected bacterial and viral infections.

13. A gel according to claim 12, wherein said cosmetically acceptable wax is lanolin.

14. A gel according to claim 12, wherein said medicament is nonoxynol-9 contained in the range of about 0.025% to about 1.0% by weight.

15. A gel according to claim 12, wherein said liquid silicone is dimethylpolysiloxane.

16. A gel according to claim 12, wherein said polypropylene glycol fatty acid ester is polypropylene glycol mono-oleate.

17. A sterilizable, hydrophilic, water-insoluble gel useful as a protective agent for skin and mucosa, consisting essentially of:
    about 50% to 90% by weight of a hydrophilic, water-insoluble, cosmetically acceptable wax;
    up to about 10% by weight of a liquid silicone water repellent agent;
    about 2% to 10% by weight of a polytetrafluoroethylene powder in microspherical form;
    up to about 10% by weight of a polypropylene glycol fatty acid ester surfactant;
    optionally, zinc oxide powder as a binding agent; and
    optionally, a medicament to fortify the gel against selected bacterial and viral infections.

* * * * *